United States Patent
Geva et al.

(10) Patent No.: US 9,615,646 B2
(45) Date of Patent: Apr. 11, 2017

(54) COSMETIC APPLICATOR WITH SPONGE TO ABSORB SUBSTANCE AND TO PREVENT LEAKAGE THEREOF

(75) Inventors: Ziv Geva, Rehovot (IL); Ayelet Mofar, Ness Ziona (IL); Ofer Leizerovich, Ness Ziona (IL)

(73) Assignee: SYNOIA TECHNOLOGIES LTD., Ness Ziona (IL)

( * ) Notice: Subject to any disclaimer, the term of this patent is extended or adjusted under 35 U.S.C. 154(b) by 0 days.

(21) Appl. No.: 13/883,016

(22) PCT Filed: Nov. 3, 2011

(86) PCT No.: PCT/IL2011/000858
§ 371 (c)(1),
(2), (4) Date: May 2, 2013

(87) PCT Pub. No.: WO2012/059923
PCT Pub. Date: May 10, 2012

(65) Prior Publication Data
US 2013/0213431 A1    Aug. 22, 2013

(51) Int. Cl.
| A45D 34/04 | (2006.01) |
| A61M 35/00 | (2006.01) |
| A61H 7/00  | (2006.01) |
| A61F 13/40 | (2006.01) |

(52) U.S. Cl.
CPC .............. *A45D 34/04* (2013.01); *A61H 7/00* (2013.01); *A61H 7/003* (2013.01); *A61M 35/006* (2013.01); *A45D 2200/1009* (2013.01); *A45D 2200/1018* (2013.01)

(58) Field of Classification Search
CPC ............ A45D 34/04; A45D 2200/1018; A45D 2200/1009; A45D 2200/1036; A61B 19/44; A61H 7/00; A61H 7/003; A61H 7/004; A61H 7/005; A61M 35/006; G06K 2017/009
USPC .................................................. 132/320, 317
See application file for complete search history.

(56) References Cited

U.S. PATENT DOCUMENTS

| 4,925,327 A  | 5/1990  | Wirt          |
| 6,982,640 B2 | 1/2006  | Lindsay et al.|
| 8,544,690 B2 | 10/2013 | Garcia        |
| 8,714,853 B2 | 5/2014  | Sutcliffe     |

(Continued)

FOREIGN PATENT DOCUMENTS

| JP | 2008525076 A | 7/2008  |
| JP | 2009268536 A | 11/2009 |

(Continued)

*Primary Examiner* — Tatiana Nobrega
(74) *Attorney, Agent, or Firm* — Browdy and Neimark, PLLC

(57) ABSTRACT

A cosmetic applicator, comprising a sponge to absorb substance and prevent leakage thereof is provided herein. The sponge having an elastic open-cell of a three-dimensional membrane structure of elastic polymer and is double over molded in combination with the rigid plastic base. The sponge has predefined density enabling to absorb the substance and skin surface having predefined thickness to prevent a spontaneous release of the substance. The substance may be squeezed out of the sponge only when applying pressure on the sponge. A Radio Frequency Identification (RFID) tag is integrated to the rigid plastic base to allow information related storage.

14 Claims, 8 Drawing Sheets

(56) References Cited

U.S. PATENT DOCUMENTS

| | | |
|---|---|---|
| 2003/0077106 A1 | 4/2003 | Weihrauch |
| 2003/0165550 A1* | 9/2003 | Rhoades .............. A45D 34/041 |
| | | 424/401 |
| 2003/0235027 A1* | 12/2003 | Smeyak et al. ............... 361/679 |
| 2005/0055787 A1 | 3/2005 | Blum et al. |
| 2007/0159336 A1 | 7/2007 | Tethrake et al. |
| 2007/0185553 A1* | 8/2007 | Kennedy ........................ 607/100 |
| 2007/0223988 A1* | 9/2007 | Gruenbacher ......... A01N 25/34 |
| | | 401/137 |
| 2008/0084312 A1* | 4/2008 | Daily ......................... 340/572.8 |
| 2009/0045416 A1* | 2/2009 | Bierhuizen et al. ............ 257/88 |
| 2009/0118684 A1* | 5/2009 | Da Silva et al. ............. 604/290 |
| 2009/0166429 A1* | 7/2009 | Aylmore ....................... 235/488 |
| 2011/0015463 A1* | 1/2011 | Legendre et al. ................. 600/9 |

FOREIGN PATENT DOCUMENTS

| | | |
|---|---|---|
| JP | 2009539529 A | 11/2009 |
| WO | 02/095675 A1 | 11/2002 |
| WO | 2012059923 A1 | 5/2012 |

\* cited by examiner

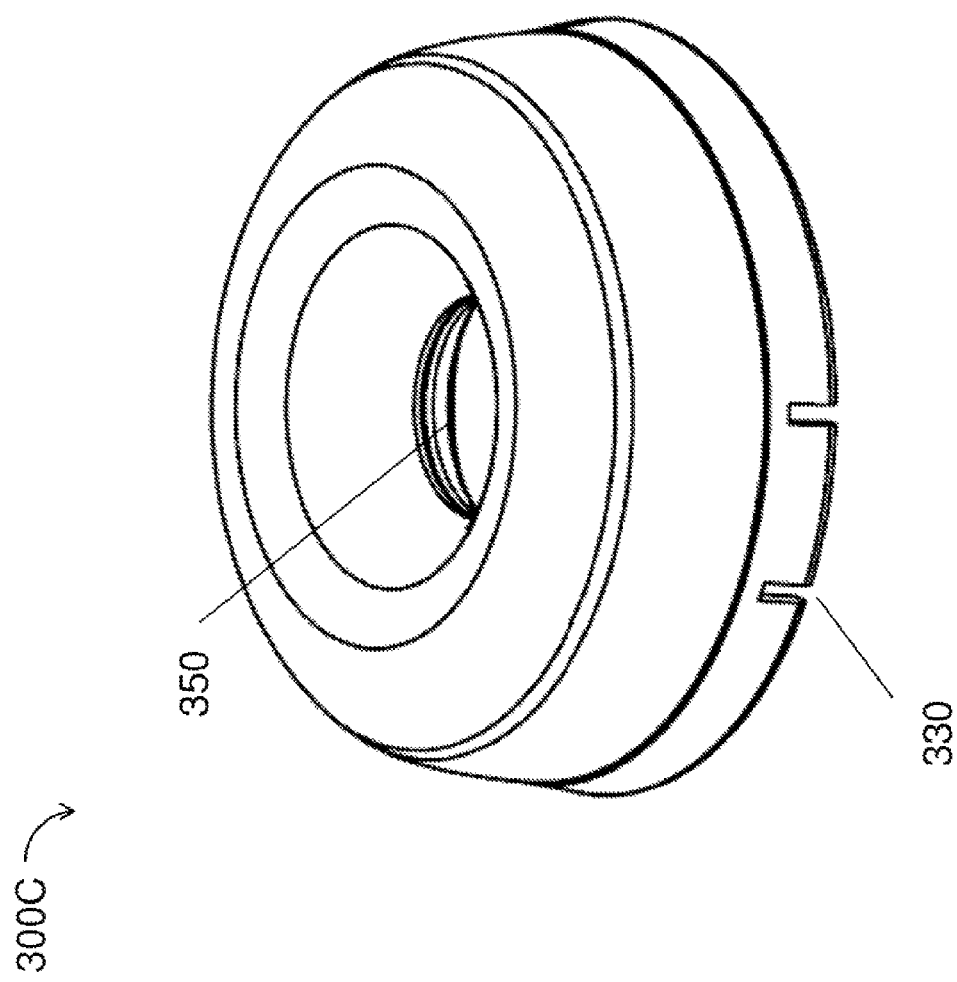

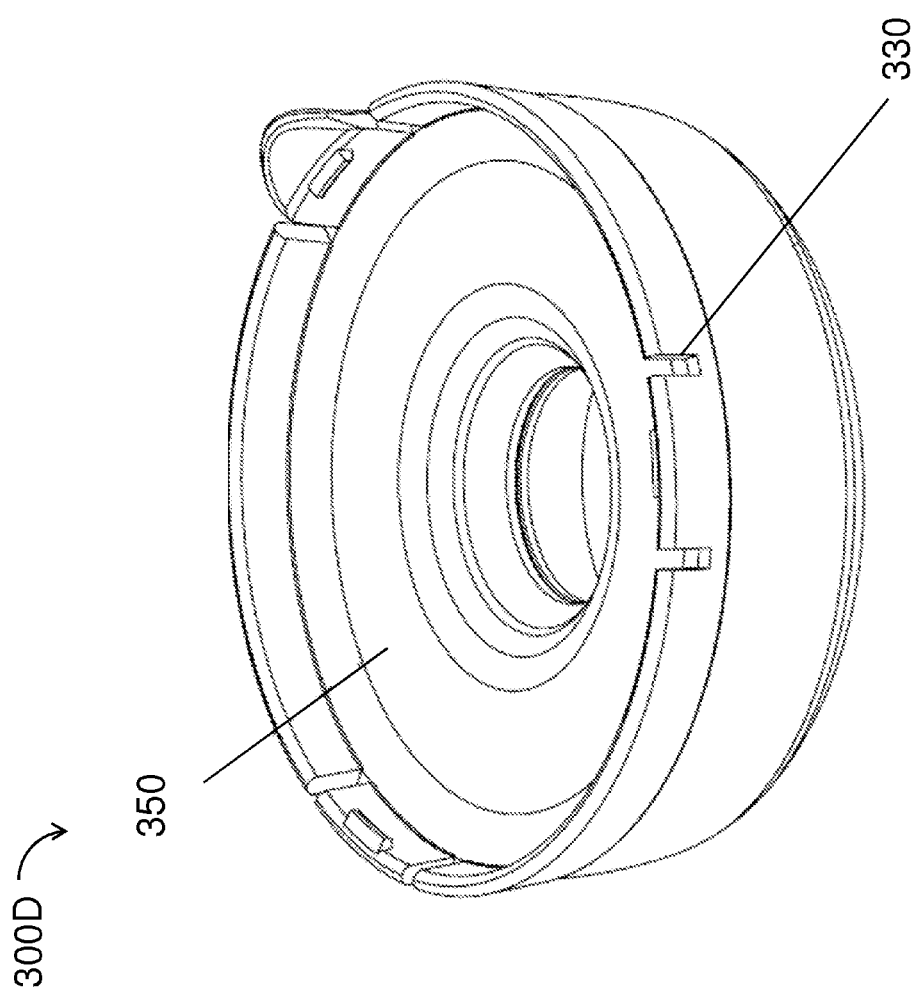

COSMETIC APPLICATOR WITH SPONGE TO ABSORB SUBSTANCE AND TO PREVENT LEAKAGE THEREOF

BACKGROUND

Technical Field

The present invention relates generally to cosmetic applicators. More particularly, the present invention relates to cosmetic applicators that are attached to a medical device.

Discussion of Related Art

Most sponges for cosmetic purposes, known in the art, are regular sponges with no additional features or value. These regular sponges do not provide useful information to a user. Useful information to the user may be, for example, information regarding suggested amount of substance in a specific treatment or duration of this treatment. Further, most sponges known in the art, are wasteful because an excessive amount of substance may be squeezed out.

BRIEF SUMMARY

The present invention provides a cosmetic applicator for absorbing a substance and prevent leakage thereof. The cosmetic applicator is comprised of: a sponge having an elastic open-cell of a three-dimensional membrane structure of elastic polymer; a rigid plastic base and a Radio Frequency Identification (RFID) tag integrated to the rigid plastic base. The sponge has predefined density enabling to absorb the substance, and the sponge has skin surface having predefined thickness to prevent a spontaneous release of the substance, such that when the substance is squeezed out of the sponge only when applying pressure on the sponge.

According to some embodiments of the present invention the skin surface is flat. According to some embodiments of the present invention the sponge is having a hollow cavity to enable insertion of treatment functional components.

According to some embodiments of the present invention the predefined density of the sponge is similar to absorption capacity of oil and water in a range between 5 cc and 7 cc.

According to some embodiments of the present invention the RFID tag is integrated during the over molding of the sponge with the rigid plastic base.

According to some embodiments of the present invention the RFID tag is initially bonded to the rigid plastic base using flip-chip bonding technology.

According to some embodiments of the present invention the sponge is double over molded in combination with the rigid plastic base.

According to some embodiments of the present invention the bonded RFID tag and the rigid plastic base are integrated through an over molding process in which thermoplastic elastomers are injected into a mold at predefined temperature to yield the cosmetic applicator including the sponge having three dimensional structure bonded to the rigid plastic base and encapsulating an RFID tag.

According to some embodiments of the present invention the level of viscosity of the substance is controlled by pressing on different spots in the sponge.

According to some embodiments of the present invention the information regarding a cosmetic treatment is stored in the RFID tag that is integrated in the cosmetic applicator.

According to some embodiments of the present invention the the information that is stored is at least one of: (i) type of treatment; (ii) expiration data of the substance; and (iii) length of cosmetic treatment.

According to some embodiments of the present invention the information that is stored is at least one of: encryption code, association code to medical device of different equipment provider, expiration date or manufacturing dates.

According to some embodiments of the present invention the RFID tag maintains information which is updated during the treatment process.

According to some embodiments of the present invention the updated information is calculated by the RFID chip.

According to some embodiments of the present invention the updated information is received from a medical device associated with said applicator.

According to some embodiments of the present invention the applicator is designed to be connected to a medical device.

The present invention provides a method to manufacture a cosmetic applicator, the method comprise the steps of: bonding a Radio Frequency Identification (RFID) tag to a rigid plastic base, integrating the bonded RFID and the rigid plastic base through a double over molding process; and injecting thermoplastic elastomers into a mold at a predefined temperature to yield a cosmetic applicator with a sponge having three dimensional structure bonded to a rigid plastic base and encapsulating the RFID tag.

According to the present invention the bonding stage is processed by using flip-chip bonding technology.

Embodiments of the present invention provide a cosmetic applicator, comprising a sponge as part of a cosmetic applicator, to absorb substance and prevent leakage thereof. The substance that is absorbed in the sponge is squeezed out of the sponge, only when applying pressure on the sponge. The sponge may have an open-cell of a three-dimensional membrane structure of elastic polymer, attached to a rigid plastic base and a Radio Frequency Identification (RFID) tag integrated to the rigid plastic base. Further, the sponge is double over molded in combination with the rigid plastic base. The sponge may have a predefined density enabling to absorb the substance. Furthermore, the sponge may have skin surface having predefined thickness to prevent a spontaneous release of the substance.

Additionally, embodiments of the present invention provide the cosmetic applicator comprising the sponge with at least one shape of skin surfaces: (i) flat; and (ii) having a hollow cavity to enable insertion of components.

According to some embodiments of the present invention the density of the sponge material after the molding process is between 40 to 250 $Kg/m^3$.

Optionally, the predefined density is similar to absorption capacity of oil and water in a range between 5 cc and 7 cc.

Furthermore, the RFID tag is integrated during the over molding of the sponge with the base and is initially bonded to the rigid plastic base using flip-chip bonding technology. Then, the bonded RFID tag and the rigid plastic base are integrated through an over molding process in which thermoplastic elastomers are injected into a mold at predefined temperature to yield a cosmetic applicator with a sponge having three dimensional structure bonded to a rigid plastic base and encapsulating an RFID tag. The RFID tag may store information regarding a cosmetic treatment for each sponge.

Embodiments of the present invention provide a cosmetic applicator with the sponge that allows control on level of viscosity of the substance that is coming out of the sponge. The control on the level of viscosity is achieved by pressing on different spots on the sponge. Further, the sponge is made of a material to enable amount of peeling powder for scrub in a range between 0.160 gram and 0.180 gram.

Additionally, embodiments of the present invention provide a method to manufacture a cosmetic applicator. The method may include the following steps: (i) bonding Radio Frequency Identification (RFID) tag to a rigid plastic base using flip-chip bonding technology; (ii) integrating the bonded RFID and the rigid plastic base through a double over molding process; and (iii) injecting thermoplastic elastomers into a mold at a predefined temperature.

These, additional, and/or other aspects and/or advantages of the present invention are: set forth in the detailed description which follows; possibly inferable from the detailed description; and/or learnable by practice of the present invention.

BRIEF DESCRIPTION OF THE DRAWINGS

The present invention will be more readily understood from the detailed description of embodiments thereof made in conjunction with the accompanying drawings of which:

FIG. 3C is an isometric view diagram of a cosmetic applicator including a sponge with a hollow cavity to enable insertion of components, according to some embodiments of the invention;

FIG. 3D is an isometric view diagram of a bottom of cosmetic applicator including a sponge with a hollow cavity to enable insertion of components, according to some embodiments of the invention;

DETAILED DESCRIPTION

Figure 1:
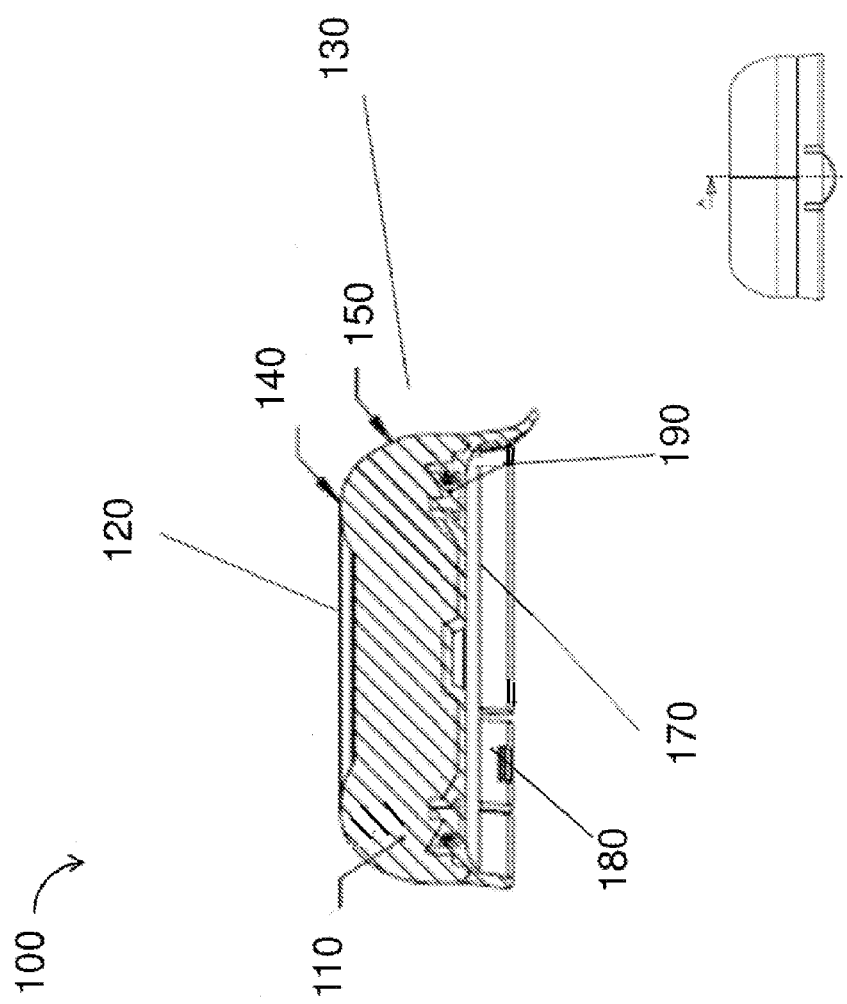
FIG. 1 is a cross sectional view diagram of a cosmetic applicator with a sponge with a flat skin surface, according to some embodiments of the invention.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Embodiments of the present invention provide a cosmetic applicator with a "clever" sponge. The "clever" sponge may store information regarding a cosmetic treatment utilizing an RFID tag integrated to a rigid plastic base in each cosmetic applicator. The cosmetic applicator may be connected to a medical device for comfortable usage. The "clever" sponge may have a hollow cavity to allow insertion of components and increase range of usage beyond substance smearing. For example, massage with or without substance.

An information regarding a cosmetic treatment is stored in the RFID tag that is integrated in the cosmetic applicator. The information that is stored includes at least one of: (i) type of treatment; (ii) expiration data of the substance; and (iii) length of cosmetic treatment.

The electronic tag may contain information for operating the applicator in association with an electronic cosmetic device.

Then information stored in the RFID tag may include encryption information for preventing unauthorized use if the applicator,' association code to medical device of different equipment provider for creating differentiation between different providers, expiration date or manufacturing dates.

According to some embodiments of the present invention the RFID tag may store information during the treatment received from the medical device attached to the applicator or optionally by the RFID chip itself, such information may include: treatment period, usage of substance or any parameters related to the process of the treatment.

According to some embodiments of the present invention the chip in RFID tag may be programmed to become in active after the expiration date of the capsule.

FIG. 1 is a cross sectional view diagram of a cosmetic applicator with a sponge having a flat skin surface, connected to a medical device, according to some embodiments of the invention.

According to an aspect of the present invention, a cosmetic applicator 100 includes a sponge 130 that may have an open-cell of a three-dimensional membrane structure of elastic polymer and a Radio Frequency Identification (RFID) tag 190 integrated to a rigid plastic base 170.

According to another aspect of the present invention, the sponge 130 in the cosmetic applicator 100 may have a predefined density enabling to absorb substance 110. For example, cream lotion or powder.

According to some embodiments of the present invention the density of the sponge material after the molding process is between 40 to 250 Kg/m³.

Optionally, the predefined density is similar to absorption capacity of oil and water in a range between 5 cc and 7 cc.

According to yet another aspect of the present invention, the sponge 130 may have skin surface 120 having predefined thickness to prevent a spontaneous release of the substance from a capsule base 180. The substance may be squeezed out of the sponge 130 only when applying pressure on the sponge 130.

According to another aspect of the present invention, the sponge 130 is double over molded in combination with a rigid plastic base 170.

In a non limiting example, a user (not shown) may wish to use a cosmetic applicator 100 with a sponge 130 for several purposes. The purposes may be: (i) conducting an anti eye-wrinkles treatment operated every other night in a gradual duration for three weeks; (ii) an oily skin treatment operated every morning with changing amount of cream for seven weeks; (iii) applying face powder every morning; and (iv) applying face powder every evening during the weekend.

According to an aspect of the present invention, the user may use a different sponge 130 for each purpose. The user may connect the sponge 130 to a cosmetic applicator 100 every night during the three weeks anti eye-wrinkles treatment. The sponge 130 may store on integrated RFID tag 190 information such as number of treatment and duration of each treatment. The user may use the information, for example, to ensure the treatment is taken every other day and to know what the required duration of each treatment is. The anti eye-wrinkles cream may be stored in the capsule base 180. The anti eye-wrinkles cream may be squeezed out of the capsule base 180 via a foam layer 150 and go out through the skin surface 120. The sponge 130 may have open-cell of a three-dimensional membrane structure of elastic polymer with a predefined thickness 140 to prevent usage of excessive amount of cream or any other substance.

According to some embodiments of the present invention the sponge is made of foam polyurethane covered by skin layer. The foam may contain cosmetic or therapeutic substance.

According to some embodiments of the present invention a lotion substance is injected inside the sponge and powder substance is absorbed in the sponge. The composition of the lotion and powder may change the viscosity of the substance, according to the treatment requirements. Optionally the powder material may be spread on the sponge surface instead of being injected for influencing the viscosity of the substance.

Further, the user may wish to conduct oily skin treatment every morning with gradually increasing amount of cream for seven weeks. For that purpose, the user may use a dedicated sponge 130 with a specific cream designated for that purpose. The cream may be put in a capsule base 180 of the sponge 130. Furthermore, the information stored in the RFID tag 190 may provide the user with information regarding the required amount of cream for each treatment or on an expiration date of the cream.

A third sponge may be used to put face powder every morning. The sponge 130 with face powder in the capsule base 180 and a fourth sponge 130 with a face powder that fits evening looks. The amount of face powder released from the sponge used in morning time may be different from the amount released during evenings during the weekends. A relevant amount of face powder is saved in the RFID tag 190.

According to yet another aspect of the present invention, the RFID tag 190 may be integrated during the double over molding of the sponge 130 with the rigid plastic base 170. Furthermore, the RFID tag 190 is initially bonded to the rigid plastic base 170 using flip-chip bonding technology. Then, at the next step, the bonded RFID tag 190 and thermoplastic elastomers may be integrated through an over molding process in which the thermoplastic elastomers are injected into a mold at predefined temperature to yield a cosmetic applicator 100 with a sponge 130 having three dimensional structure bonded to a rigid plastic base 170 and encapsulating an RFID tag 190.

In a non limiting example, a user with a beard on his face may wish to apply a cream with higher level of velocity on the hairy parts and low to medium level of viscosity cream on the less hairy parts on his face. According to yet another aspect of the invention, in order to control the level of viscosity of the cream that is coming out of the capsule base 180 the user may press on different spots on the sponge 130. From each spot on the sponge 130 an amount of cream in different levels of viscosity may come out.

Figure 2:
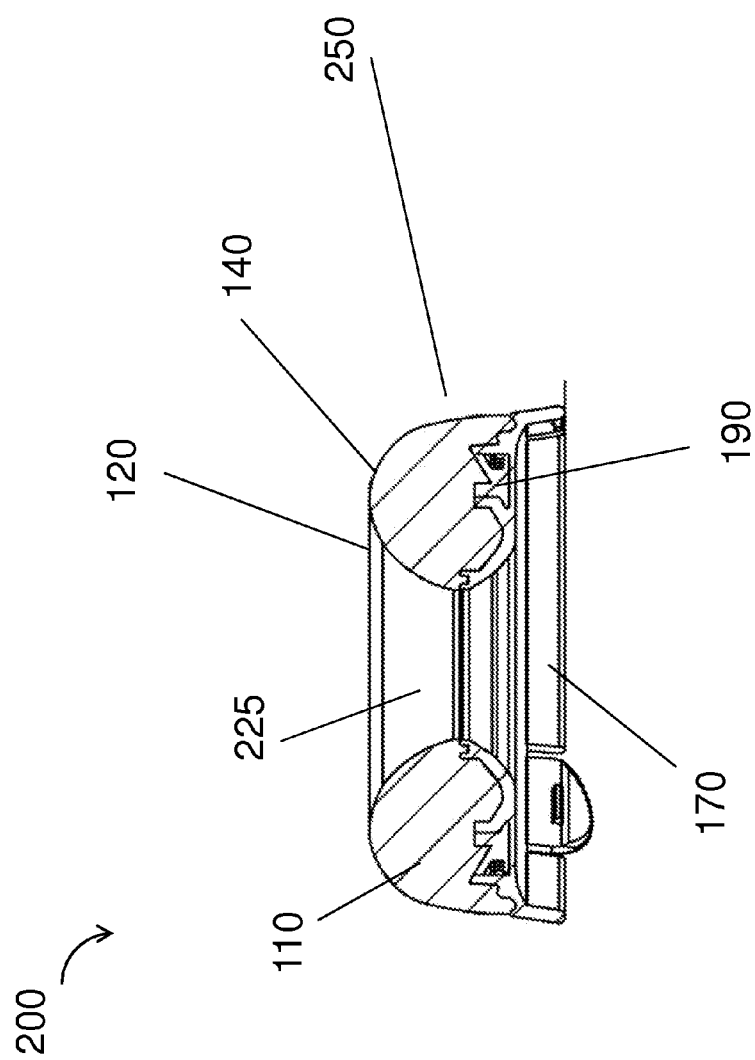
FIG. 2 is a cross sectional view diagram of a cosmetic applicator including a sponge with a hollow cavity to enable insertion of components, according to some embodiments of the invention.

FIG. 2 is a cross sectional view diagram of a cosmetic applicator with a sponge including a hollow cavity to enable insertion of components, according to some embodiments of the invention.

According to an aspect of the present invention, a hollow cavity 225 in sponge 250 may be used to insert essential components utilized for various treatments. The components may be Light Emitting Diode (LED) or dedicated components for specific treatments. The cosmetic applicator 200 connected to a medical device (not shown) may be used with or without additional substance such as cream, lotion or powder.

Figure 3A:
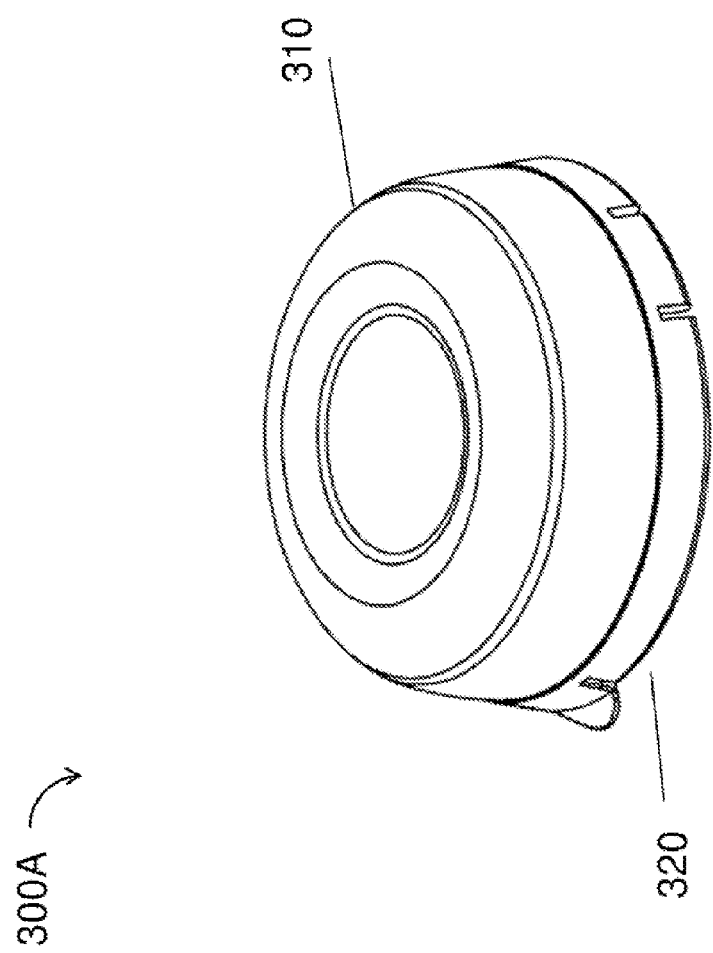
FIG. 3A is an isometric view diagram of a cosmetic applicator including a sponge with a flat skin. surface, according to some embodiments of the invention.

FIG. 3A is an isometric view diagram of a cosmetic applicator including a sponge with a flat skin surface, according to some embodiments of the invention.

According to an aspect of the present invention, the cosmetic applicator 300A may have a flat skin surface 310. A capsule (not shown) with substance may be attached to the bottom of the cosmetic applicator 320 and may release the substance when the cosmetic applicator 300A is connected to a medical device (not shown).

Figure 3B:
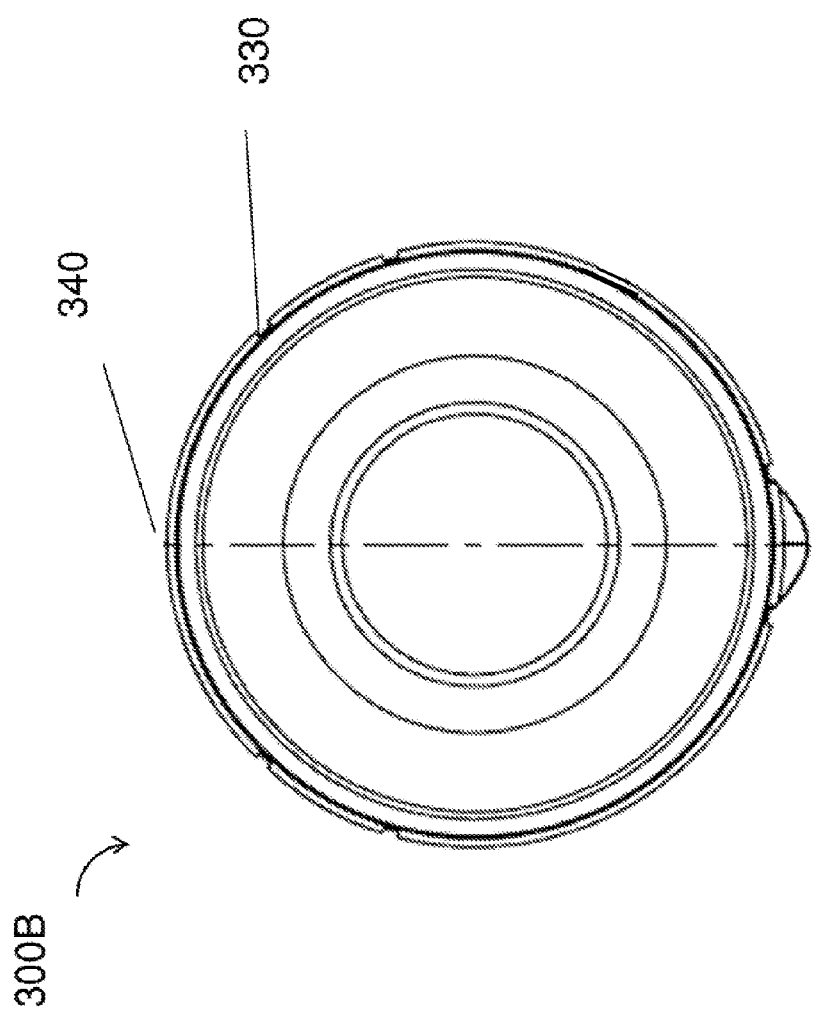
FIG. 3B is a top view diagram of a cosmetic applicator, according to some embodiments of the invention.

FIG. 3B is a top view diagram of a bottom of a cosmetic applicator, according to some embodiments of the invention.

According to an aspect of the present invention, there may be a plurality of grippers, for example. gripper 330 at the bottom of the cosmetic applicator 300B to attach to a capsule with a substance and connect to a medical device (not shown). Mid-line 340 is a section cut of cosmetic applicator 100 in FIG. 1.

FIG. 3C is an isometric view diagram of a cosmetic applicator including a sponge with a hollow cavity to enable insertion of components, according to some embodiments of the invention.

According to an aspect of the present invention, the cosmetic applicator 300C may have a hollow cavity 350. The hollow cavity 350 may allow insertion of therapeutic component when connected to a medical device (not shown) to aid in immersing substance or to operate a treatment with no substance.

FIG. 3D is an isometric view diagram of a bottom of cosmetic applicator including a sponge with a hollow cavity to enable insertion of components, according to some embodiments of the invention.

According to an aspect of the present invention, hollow cavity 350 may allow insertion of components. Gripper 330 may allow a capsule with substance to connect to the cosmetic applicator 300D.

Figure 4A:
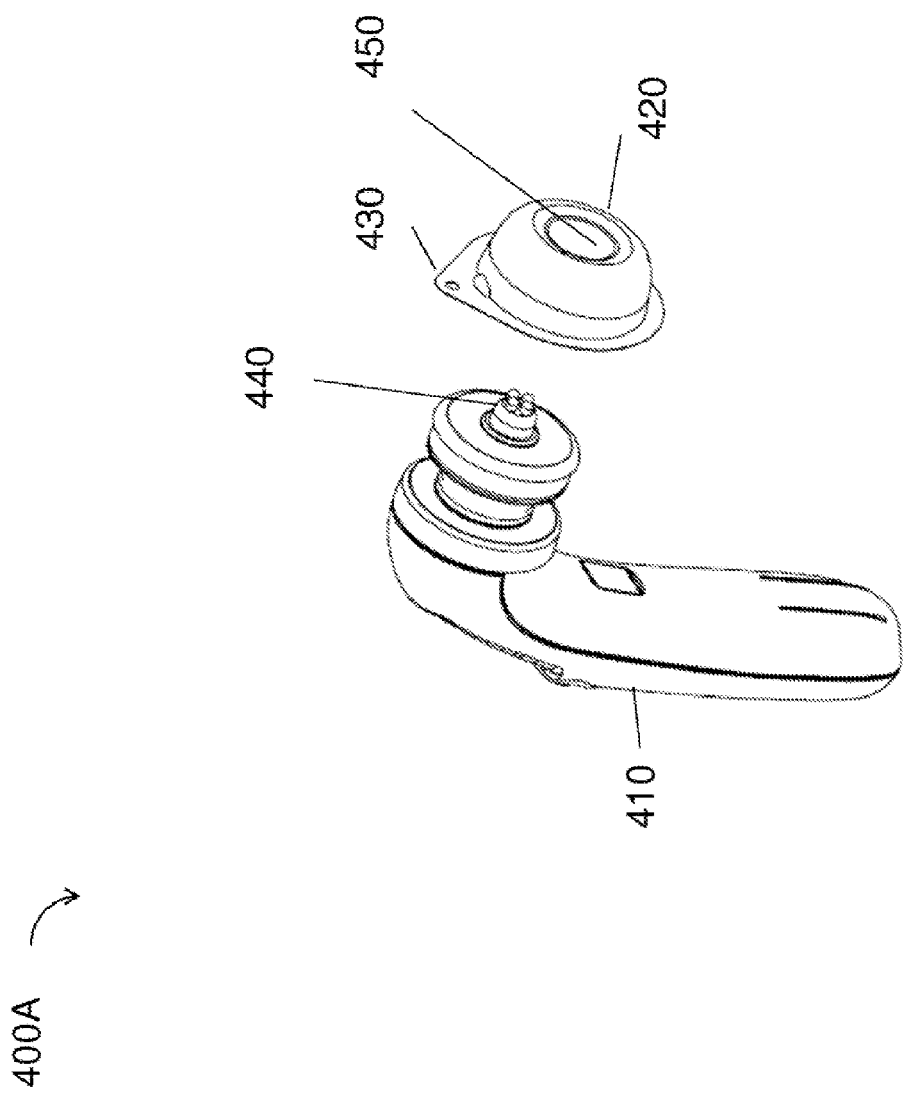
FIG. 4A is an isometric view diagram of a cosmetic applicator connected to a medical device and an unplugged capsule connected to the cosmetic applicator, according to some embodiments of the invention.

FIG. 4A is an isometric view diagram of a cosmetic applicator connected to a medical device and an unplugged capsule connected to the cosmetic applicator, according to some embodiments of the invention.

According to an aspect of the present invention, the cosmetic applicator 400A is designed with a hollow cavity 450 to allow insertion of components 440 which may be connected to a medical device 410. The sponge of the cosmetic applicator may have a hollow cavity 450 and may have a capsule 430 connected to it at the bottom.

Figure 4B:
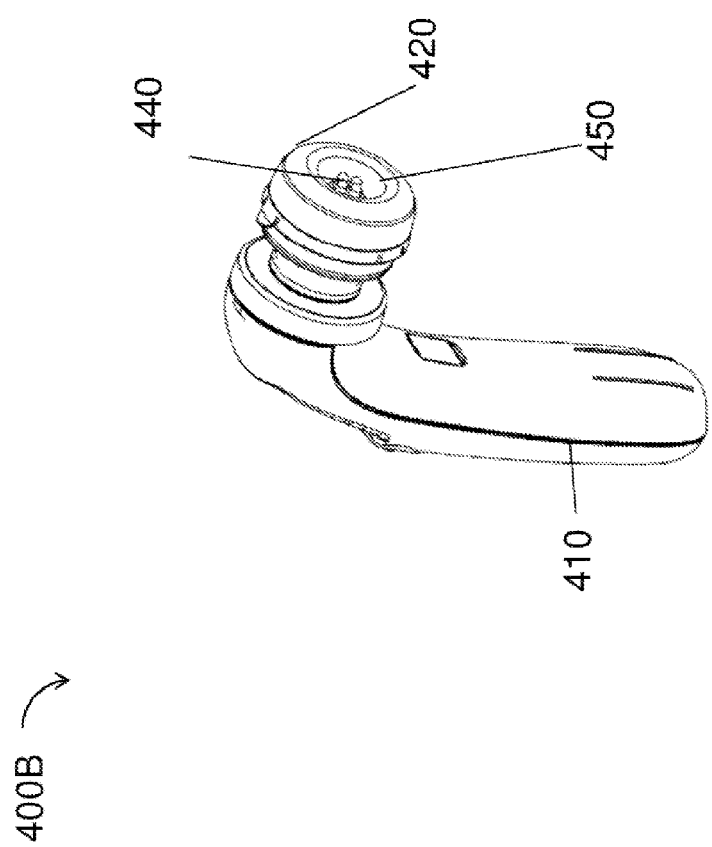
FIG. 4B is an isometric view diagram of a cosmetic applicator connected to a medical device and a capsule connected to the cosmetic applicator, according to some embodiments of the invention.

FIG. 4B is an isometric view diagram of a cosmetic applicator connected to a medical device and a capsule connected to the cosmetic applicator, according to some embodiments of the invention.

According to an aspect of the present invention, the cosmetic applicator 400B may have a skin surface 420 with a hollow cavity 450 to allow insertion of components 440. The cosmetic applicator 400B may be connected to a medical device 410.

In the above description, an embodiment is an example or implementation of the invention. The various appearances of "one embodiment", "an embodiment" or "some embodiments" do not necessarily all refer to the same embodiments.

Although various features of the invention may be described in the context of a single embodiment, the features may also be provided separately or in any suitable combination.

Conversely, although the invention may be described herein in the context of separate embodiments for clarity, the invention may also be implemented in a single embodiment.

Furthermore, it is to be understood that the invention can be carried out or practiced in various ways and that the invention can be implemented in embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

What is claimed is:

1. A cosmetic/medical applicator for storing and applying a substance, the applicator comprising:
    a sponge having an elastic open-cell three-dimensional membrane structure of elastic polymer covered by a sponge skin surface defining a top surface of the sponge, where a cosmetic or medical substance is injected into the sponge such that the sponge serves as a container to include all of the substance to be used, the substance is provided in a specific amount required for a pre-determined treatment, the sponge having a shape providing a central through-hole;
    a rigid base bonded to an entire bottom surface of the sponge, such that the rigid base has a shape complementary to the shape of the sponge and provides a bonding surface interfacing with the sponge, a planar bottom surface opposite the bonding surface and a central through-hole of the rigid base being aligned with the central through-hole of the sponge, wherein the rigid base is an integral part of the applicator, and the planar bottom surface is configured to abut against the medical device; and
    a Radio Frequency Identification (RFID) tag containing information regarding a cosmetic or medical treatment embedded or attached to the rigid base such that the RFID tag is positioned between the bottom surface of the sponge and the planar bottom surface of the rigid base and no portion of the RFID tag extends below the planar bottom surface of the rigid base in a direction away from the sponge,
    wherein the sponge and the sponge skin surface have a predetermined density and thickness, respectively, sufficient to enable injection of the substance into the sponge while preventing a spontaneous release of the substance, such that a required amount of the substance is squeezed out only when pressure is applied to the sponge.

2. The applicator according to claim 1, wherein the central through-hole of the sponge defines a hollow cavity to enable insertion of functional treatment components when the applicator is coupled to the medical device.

3. The applicator according to claim 1, wherein the predefined density of the sponge is similar to absorption capacity of cosmetic or medical substances including at least one of oil and water in a range between 5 cc and 7 cc.

4. The applicator according to claim 1 wherein the density of the sponge material after the molding process is between 40 to 250 Kg/m3.

5. The applicator according to claim 1, wherein the RFID tag is embedded during the over molding of the sponge with the rigid plastic base.

6. The applicator according to claim 1, wherein the RFID tag is initially bonded to the rigid base.

7. The applicator according to claim 1 wherein the sponge is double over molded in combination with the rigid base.

8. The applicator according to claim 5, wherein the bonded RFID tag and the rigid base are integrated through an over molding process in which thermoplastic elastomers are injected into a mold at predefined temperature to yield the cosmetic applicator including the sponge bonded to the rigid base and encapsulating the RFID tag.

9. The applicator according to claim 1, wherein control on level of viscosity of the substance is enabled by pressing on different spots in the sponge.

10. The applicator according to claim 1, wherein the information that is stored is at least one of: (i) type of treatment; (ii) expiration date of the substance; and (iii) length of treatment.

11. The applicator according to claim 1, wherein the information that is stored is at least one of: encryption code, association code to medical device of different equipment provider, expiration date or manufacturing dates.

12. The applicator according to claim 1, wherein the RFID tag maintains information which is updated during the treatment process.

13. The applicator according to claim 12 wherein the updated information is calculated by the RFID chip tag.

14. The applicator according to claim 12 wherein the updated information is received from a medical device associated with said applicator.

* * * * *